United States Patent
Peitz et al.

(10) Patent No.: US 11,952,340 B2
(45) Date of Patent: Apr. 9, 2024

(54) PROCESS FOR REMOVING POLYUNSATURATED HYDROCARBONS FROM C4 HYDROCARBON STREAMS IN THE PRESENCE OF MERCAPTANS, DISULFIDES AND C5 HYDROCARBONS

(71) Applicant: Evonik Oxeno GmbH & Co. KG, Marl (DE)

(72) Inventors: Stephan Peitz, Der-Erkenschwick (DE); Guido Stochniol, Haltern am See (DE); Markus Winterberg, Waltrop (DE); Jörg Schallenberg, Dorsten (DE); Armin Matthias Rix, Marl (DE); Andreas Wolff, Recklinghausen (DE)

(73) Assignee: Evonik Oxeno GmbH & Co. KG, Marl (DE)

(*) Notice: Subject to any disclaimer, the term of this patent is extended or adjusted under 35 U.S.C. 154(b) by 45 days.

(21) Appl. No.: 16/713,301

(22) Filed: Dec. 13, 2019

(65) Prior Publication Data
US 2020/0216376 A1    Jul. 9, 2020

(30) Foreign Application Priority Data
Jan. 8, 2019 (EP) ..................... 19150659

(51) Int. Cl.
*C07C 7/163* (2006.01)
*B01J 19/00* (2006.01)
*C07C 5/05* (2006.01)
*C07C 7/00* (2006.01)

(52) U.S. Cl.
CPC .......... *C07C 7/163* (2013.01); *B01J 19/0006* (2013.01); *C07C 5/05* (2013.01); *C07C 7/005* (2013.01); *B01J 2219/00038* (2013.01); *B01J 2219/0004* (2013.01); *B01J 2219/00162* (2013.01); *C07C 2523/42* (2013.01); *C07C 2523/44* (2013.01)

(58) Field of Classification Search
None
See application file for complete search history.

(56) References Cited

U.S. PATENT DOCUMENTS

| | | | |
|---|---|---|---|
| 6,919,016 B2* | 7/2005 | Podrebarac | C07C 2/12 |
| | | | 208/16 |
| 7,939,597 B2 | 5/2011 | Bub et al. | |
| 8,198,481 B2 | 6/2012 | Kuppinger et al. | |
| 8,258,249 B2 | 9/2012 | Bub et al. | |
| 8,293,941 B2 | 9/2012 | Kuppinger et al. | |
| 8,481,784 B2 | 7/2013 | Kuppinger et al. | |
| 8,524,945 B2 | 9/2013 | Stochniol et al. | |
| 8,859,834 B2 | 10/2014 | Boeing et al. | |
| 8,895,683 B2 | 11/2014 | Kuppinger et al. | |
| 9,856,184 B2 | 1/2018 | Stochniol et al. | |
| 10,189,755 B2 | 1/2019 | Reeker et al. | |
| 10,196,327 B2 | 2/2019 | Stochniol et al. | |
| 10,227,279 B2 | 3/2019 | Stochniol et al. | |
| 2005/0010071 A1 | 1/2005 | Podrebarac et al. | |
| 2006/0276334 A1 | 12/2006 | Balduf et al. | |
| 2009/0068440 A1 | 3/2009 | Bub et al. | |
| 2013/0172641 A1 | 7/2013 | Boeing et al. | |
| 2015/0166475 A1* | 6/2015 | Peitz | C07C 319/18 |
| | | | 568/59 |
| 2019/0283003 A1 | 9/2019 | Nadolny et al. | |
| 2019/0283004 A1 | 9/2019 | Nadolny et al. | |
| 2019/0283005 A1 | 9/2019 | Nadolny et al. | |
| 2019/0283006 A1 | 9/2019 | Nadolny et al. | |

FOREIGN PATENT DOCUMENTS

| | | | | |
|---|---|---|---|---|
| EP | 0288362 A1 * | 10/1988 | ........... | C07C 5/2556 |
| EP | 2 590 913 A1 | 5/2013 | | |
| TW | 201420557 | 6/2014 | | |
| WO | 2012/004081 A1 | 1/2012 | | |
| WO | 2014/209736 A1 | 12/2014 | | |

OTHER PUBLICATIONS

Machine translation EP 0288362. Retrieved Jun. 9, 2023 (Year: 2023).*
Nadolny et al., U.S. Appl. No. 16/509,532, filed Jul. 12, 2019.
European Search Report dated Jul. 10, 2019 in EP 19150659.1 (6 pages).
Substantive Examination Adverse Report (Section 30(1)) dated Jun. 16, 2022 in MY Application No. PI2020000062 (5 pages).
Singapore Search Report completed on Jul. 22, 2022 in SG 102020000057U (3 pages).
Peitz et al., U.S. Appl. No. 18/191,139, filed Mar. 28, 2023.
U.S. Appl. No. 18/191,139, filed Mar. 28, 2023.

* cited by examiner

*Primary Examiner* — In Suk C Bullock
*Assistant Examiner* — Alyssa L Cepluch
(74) *Attorney, Agent, or Firm* — Grüneberg and Myers PLLC

(57) ABSTRACT

The present invention provides a two-stage process for removing polyunsaturated hydrocarbons from C4 hydrocarbon streams that, in addition to C4 hydrocarbons, also contain C5 hydrocarbons and mercaptans and/or disulfides.

25 Claims, No Drawings

PROCESS FOR REMOVING POLYUNSATURATED HYDROCARBONS FROM C4 HYDROCARBON STREAMS IN THE PRESENCE OF MERCAPTANS, DISULFIDES AND C5 HYDROCARBONS

CROSS REFERENCE TO RELATED APPLICATIONS

This application is a 35 U.S.C. § 119 patent application which claims the benefit of European Application No. 19150659.1 filed Jan. 8, 2019, which is incorporated herein by reference in its entirety.

FIELD

The invention relates to a two-stage process for removing polyunsaturated hydrocarbons from C4 hydrocarbon streams that, in addition to C4 hydrocarbons, also contain C5 hydrocarbons and mercaptans and/or disulfides.

BACKGROUND

Olefin-containing C4 hydrocarbon streams used in the petrochemical industry are typically C4 hydrocarbon mixtures from catalytic crackers (FCC C4) or steam crackers (crack C4). Blends of C4 hydrocarbon mixtures of different origin (C4 cut) may also be used in petrochemical processes. In addition to the n-butenes 1-butene, cis-2-butene and trans-2-butene, isobutene and the homologous alkanes butane and isobutane, industrial C4 hydrocarbon mixtures such as the abovementioned mixtures also typically contain polyunsaturated compounds, in particular 1,3-butadiene, but-3-en-1-yne and 1,2-butadiene. Before the C4 hydrocarbon mixtures are made available for processes such as oligomerization or before individual compounds may be isolated from the C4 mixtures, it is often necessary to remove the polyunsaturated hydrocarbons.

C4 hydrocarbon mixtures from steam crackers or catalytic crackers may contain high proportions of polyunsaturated compounds, in particular high proportions (40%+ by weight) of 1,3-butadiene. Workup then initially begins with reducing the content of polyunsaturated compounds, for example through extractive distillation, to values of less than or equal to 1% by weight based on the overall composition of the C4 hydrocarbon mixture. The resulting mixture containing only small residual amounts of butadiene is also referred to as raffinate I, from which isobutene can then be removed to produce raffinate II.

Further workup typically then comprises a further step for the (almost) complete removal of the polyunsaturated hydrocarbons. EP 2 590 913 A1 discloses in this regard a selective hydrogenation of the polyunsaturated hydrocarbons still present in the presence of hydrogen. To avoid unwanted side reactions and equipment states, the hydrogen that is needed must be present as a homogeneous solution dissolved in the C4 feed mixture. However, there is an upper limit on the solubility of hydrogen in C4 hydrocarbon mixtures that imposes a restriction on the maximum content of polyunsaturated hydrocarbon permitted in the inflow for the selective hydrogenation or, to be more exact, on the amount of polyunsaturated hydrocarbons that can be (selectively) hydrogenated by the maximum amount of hydrogen that can be dissolved.

To achieve (almost) complete conversion of the polyunsaturated hydrocarbons, the C4 hydrocarbon mixtures used must contain only the maximum amount of polyunsaturated hydrocarbons that can be hydrogenated with the maximum amount of hydrogen that can be dissolved. This is problematic for industrial processes in that the composition of the C4 hydrocarbon mixtures used is subject to natural fluctuations that are difficult to absorb with such a limitation on the maximum amount of polyunsaturated hydrocarbons.

SUMMARY

The object of the present invention was therefore to provide a process that can respond more flexibly to fluctuations in the amount of polyunsaturated hydrocarbons and that makes it possible for potentially larger amounts of polyunsaturated hydrocarbons to be removed from the C4 hydrocarbon streams.

The underlying object of the present invention is achieved by the process according to claim 1. Preferred embodiments are specified in the dependent claims.

DETAILED DESCRIPTION

The process according to the invention is a two-stage process for removing polyunsaturated hydrocarbons from olefin-containing C4 hydrocarbon streams that, in addition to C4 hydrocarbons, also contain C5 hydrocarbons in the range between 0.01 and 5% by weight and mercaptans and/or disulfides in the range between 0.01 and 200 ppm by weight. In the first step, at least some of the polyunsaturated hydrocarbons from the olefin-containing C4 hydrocarbon stream is hydrogenated and/or reacts with the mercaptans and/or disulfides from the olefin-containing C4 hydrocarbon stream in a first reaction zone, which consists of one or more reactors connected in parallel and/or in series, wherein the first step is carried out using a first catalyst in the presence of hydrogen and in the absence of carbon monoxide and wherein not more than 80 mol % of the available polyunsaturated hydrocarbons from the C4 hydrocarbon stream is hydrogenated and/or reacts in the first step. In a preferred embodiment, some of the polyunsaturated hydrocarbons is hydrogenated and some reacts with the mercaptans and/or disulfides from the olefin-containing C4 hydrocarbon stream. Here too, the maximum amount of 80 mol % of polyunsaturated hydrocarbons to be reacted is not exceeded. The mercaptans are preferably removed from the olefin-containing C4 hydrocarbon stream to a level below the detection limit.

After the first step and before the second step, at least one removal of high boilers takes place, wherein in particular the reaction products formed in the reaction of the polyunsaturated hydrocarbons with the mercaptans and/or disulfides and optionally at least some of the C5 hydrocarbons are removed from the C4 hydrocarbon stream.

In the second step of the process according to the invention, the polyunsaturated hydrocarbons in the olefin-containing C4 hydrocarbon stream that did not react in the first step are selectively hydrogenated using a second catalyst in the presence of hydrogen and carbon monoxide in a second reaction zone, which consists of one or more reactors connected in parallel and/or in series. The catalyst used in the first step and the catalyst used in the second step are different from one another.

The process according to the invention has the advantage that in the first step not only is it possible for at least some of the polyunsaturated hydrocarbons, in particular 1,3-butadiene and/or 1,2-butadiene and/or but-3-en-1-yne to be hydrogenated, but it is also possible for mercaptans and/or disulfides, which are present in industrial C4 hydrocarbon mixtures in very small amounts and must be removed because of their ability to damage the catalysts in subsequent processes, to react and then be removed. The maximum permitted amount of polyunsaturated hydrocarbons in the olefin-containing C4 hydrocarbon stream undergoing purification is consequently almost twice as high compared with selective hydrogenation. The concentration of polyunsaturated hydrocarbons in industrial C4 hydrocarbon streams is subject to process-related fluctuations. These fluctuations in the concentration of polyunsaturated hydrocarbons in the industrial C4 hydrocarbon stream can thus be absorbed much more easily by the process according to the invention.

The first step, i.e. the hydrogenation of the polyunsaturated hydrocarbons and/or the reaction of the polyunsaturated hydrocarbons with the mercaptans and/or disulfides in the C4 hydrocarbon stream, takes place in the presence of hydrogen. To prevent side reactions such as full hydrogenation to alkanes or isomerization of the double bond in 1-olefins to internal olefins, the amount of hydrogen used in the first step should not be too high. The molar ratio of hydrogen to polyunsaturated hydrocarbons in the first step is preferably between 0.01 and 0.8, more preferably between 0.1 and 0.5. The hydrogen can be metered into the reaction zone separately from the incoming C4 hydrocarbon stream or it can be added to the incoming C4 hydrocarbon stream beforehand; a homogeneous mixture of C4 hydrocarbon stream and hydrogen must be present in the reactor.

The first step of the process according to the invention is moreover carried out in the absence of carbon monoxide. This means that no carbon monoxide is added to the C4 carbon stream. However, very small amounts of carbon monoxide potentially present as impurities in industrial hydrocarbon streams may be present, since they cannot be removed without considerable effort.

In the first step of the process according to the invention, heterogeneous catalysts containing at least two metals of the 10th group of the periodic table, preferably palladium and platinum, may be used as the first catalyst. The metals may be present partly in the form of their oxide as a result of calcination. The metals are preferably present on a support material. The support material is selected from the group consisting of alumina, silica gel and activated carbon, wherein alumina is preferably used as support material. In a particularly preferred embodiment, a shell catalyst is used as the first catalyst, which comprises alumina as support material and palladium and platinum as metals and wherein the catalyst has a palladium concentration of up to 2.0% by weight, preferably of up to 1.0% by weight, more preferably of up to 0.5% by weight and a platinum concentration of up to 1.0% by weight, preferably of up to 0.5% by weight, more preferably of up to 0.2% by weight. The concentration of palladium should be at least a factor of 2 higher than that of platinum.

The first catalyst preferably has a specific surface area of from 50 to 400 $m^2/g$, more preferably from 100 to 300 $m^2/g$, particularly preferably from 200 to 300 $m^2/g$, which can be determined by gas adsorption in accordance with DIN ISO 9277 (status: last updated 2014-01).

The inlet temperature of the olefin-containing C4 hydrocarbon stream entering the reactor(s) of the first reaction zone in the first step is preferably in the range from 0 to 180° C., more preferably in the range from 60 to 150° C. and particularly preferably in the range from 80 to 130° C. The pressure in the first step is preferably in the range from 2 to 50 bar, more preferably in the range from 6 to 40 bar and particularly preferably in the range from 10 to 30 bar.

The hydrogenation and/or reaction in the first step is preferably operated as a liquid-phase process, which means that all components in the first reaction zone, i.e. in the at least one reactor, are present in the liquid phase or are introduced into the first reaction zone in liquid form. Suitable reactors for carrying out the reaction in the first step are fixed-bed reactors or tube-bundle reactors. Preferably, the hydrogen has been completely dissolved in the liquid phase. It is clear that the temperature and pressure must then be chosen so that the hydrogen remains completely dissolved and does not give rise to a gas phase upstream of and in the reaction zone. Hydrogen should accordingly be added to the olefin-containing C4 hydrocarbon stream in finely dispersed form and in amounts such that the liquid phase is always homogeneous upstream of and in the reaction zone. There is no addition of carbon monoxide. The hydrogenation and/or reaction in the first step is moreover preferably carried out in just one reactor, i.e. the first reaction zone preferably consists of just one reactor.

After the hydrogenation of the polyunsaturated hydrocarbons and/or the reaction of the polyunsaturated hydrocarbons with the mercaptans and/or disulfides in the first step, it is possible to remove the reaction products as part of a removal of high boilers that takes place between the first and the second step. The removal is preferably carried out by means of distillation. The high boilers present in the C4 hydrocarbon stream, such as C5 hydrocarbons, can be removed at least in part together with the reaction products. The high boilers, i.e. reaction products and C5 hydrocarbons, are drawn off via the bottoms of the distillation column; the purified C4 hydrocarbon stream is drawn off at the top of the distillation column and fed into the second step. Before carrying out the second step, further process steps in which there is no interference from the polyunsaturated hydrocarbons may be carried out, for example the synthesis of MTBE (through which isobutene may be removed) or the synthesis of TBA.

A distillation column preferably used in the removal of high boilers preferably has 40 to 150 theoretical plates, more preferably 40 to 100 theoretical plates and particularly preferably 50 to 80 theoretical plates. The reflux ratio may be between 0.5 and 5, particularly preferably between 1 and 2.5, depending on the available number of plates, the composition of the feed and the required purity of the top and bottom product. The reflux ratio is defined here as the reflux mass flow divided by the mass flow of the top product (distillate).

The distillation column for the removal of high boilers is preferably operated at a pressure of 1 to 20 bar (absolute), more preferably of 5 to 12 bar (absolute). Depending on the available operating pressure, the condensation may be effected against cooling brine, cooling water or air. The bottom product, i.e. the high boilers, can be thermally utilized or used as a starting material for other processes, for example in a synthesis gas plant.

After removal of high boilers, the C4 hydrocarbon mixture, which still contains polyunsaturated hydrocarbons, is fed into the second step of the process according to the invention, i.e. the selective hydrogenation. In the second step, hydrogen is likewise added, but this time it is not substoichiometric as in the first step, but at least equimolar to the molar amount of polyunsaturated hydrocarbons present in the inflow for the second step. The molar ratio of hydrogen to the polyunsaturated hydrocarbons is in particular in the range from 2:1 to 1:1 (hydrogen to polyunsaturated hydrocarbons), preferably in the range from 1.5:1 to 1:1 and more preferably in the range from 1.2:1 to 1:1. The hydrogen can be metered into the reactor(s) of the second reaction zone separately from the incoming C4 hydrocarbon stream or it can be added to the incoming C4 hydrocarbon stream beforehand.

In the second step, carbon monoxide is additionally added to the C4 hydrocarbon stream. The content of carbon monoxide in the C4 hydrocarbon stream in the inflow of the second reaction zone is preferably between 0.05 and 20 ppm carbon monoxide, more preferably between 0.5 and 5 ppm, in each case based on the total amount of the C4 hydrocarbon stream. The carbon monoxide can be metered into the second reaction zone separately from the incoming C4 hydrocarbon stream or it can be added to the incoming C4 hydrocarbon stream beforehand.

In the second step of the process according to the invention, heterogeneous catalysts containing a single metal of the 10th group of the periodic table, preferably palladium, may be used as the second catalyst. The metal may be present partly in the form of its oxide as a result of calcination. The palladium is preferably present on a support material. The support material is selected from the group consisting of alumina, silica gel and activated carbon, wherein alumina is preferably used as support material. The concentration of the metal in the second catalyst may be 0.01 to 3% by weight, preferably 0.1 to 1% by weight, more preferably 0.3 to 0.5% by weight, in each case based on the total amount of catalyst. The second catalyst is according to the invention different from the first catalyst.

The second catalyst preferably has a specific surface area of from 50 to 400 m$^2$/g, more preferably from 100 to 300 m$^2$/g, particularly preferably from 200 to 300 m$^2$/g, which can be determined by gas adsorption in accordance with DIN ISO 9277 (status: last updated 2014-01).

The inlet temperature of the C4 hydrocarbon stream in the inflow of the second reaction zone is typically in the range from 0 to 100° C., preferably in the range from 20 to 80° C., more preferably in the range from 30 to 60° C. The pressure is typically in the range from 2 to 50 bar, preferably in the range from 6 to 30 bar, more preferably in the range from 10 to 25 bar.

The selective hydrogenation in the second step is preferably operated as a liquid-phase process, i.e. all components in the second reaction zone are present in the liquid phase or are introduced into the second reaction zone in liquid form. Suitable reactors for carrying out the selective hydrogenation are fixed-bed reactors or tube-bundle reactors. Preferably, the hydrogen and the carbon monoxide have both been dissolved completely in the liquid phase. It is clear that the temperature and pressure must then be chosen so that the hydrogen and the carbon monoxide remain completely dissolved and do not give rise to a gas phase upstream of and in the reaction zone.

The selective hydrogenation in the second step can be operated in a single stage, i.e. using a single reactor in the second reaction zone. The selective hydrogenation is preferably operated in more than one stage, i.e. using at least two reactors connected in parallel or in series in the second reaction zone, which means that the second reaction zone consists of at least two reactors connected in parallel or in series. The reactors are preferably connected in series in the second reaction zone. The hydrogen is fed into each of the reactors connected in series in the second reaction zone together with the C4 hydrocarbon stream, whereas the carbon monoxide is added only to the first of the reactors connected in series in the second reaction zone, but not to the second or subsequent reactors.

In another embodiment of the process according to the invention, the second reaction zone consists of at least three reactors. The first two reactors may be connected in parallel and both connected to the third reactor in series. Into the first two reactors, which are connected in parallel, is metered preferably hydrogen and carbon monoxide, whereas in the third reactor only hydrogen is added.

Example 1

Into a first reactor filled with 600 ml of a hydrogenation catalyst (0.5% by weight of Pd, 0.2% by weight of Pt on Al$_2$O$_3$) and heated to 90° C. is passed at 4 kg/h a C4 mixture liquefied at a pressure of 22 bar that consists of 0.7% by weight of 1,3-butadiene, 19.9% by weight of 1-butene, 38.0% by weight of 2-butenes, 29.3% by weight of isobutene and 11.3% by weight of butanes, and also 0.8% by weight of C5 hydrocarbons. The stream contains about 4 ppm by weight of dimethyl disulfide, about 3 ppm by weight of ethanethiol and about 0.5 ppm by weight of methanethiol.

Into this C4 mixture is metered an H2 stream of 9.3 Nl/h. About 73% of the butadiene present in the employed C4 mixture reacts. The resulting composition of the outflow from the first reactor is 0.2% by weight of butadiene, 20.2% by weight of 1-butene, 38.2% by weight of 2-butene, 29.3% by weight of isobutene and 11.3% by weight of butanes, and also 0.8% by weight of C5 hydrocarbons. Mercaptans and disulfides were no longer detectable in the stream.

After removal of high boilers and removal of most of the isobutene through MTBE synthesis, the stream has the following composition: 0.3% by weight of butadiene, 28.6% by weight of 1-butene, 54.0% by weight of 2-butene, 1.1% by weight of isobutene and 16.0% by weight of n-butane. This stream is liquefied at a pressure of 12 bar and passed at 4 kg/h into a second reactor filled with 600 ml of a hydrogenation catalyst (0.5% by weight of Pd on Al$_2$O$_3$ and heated at 40° C. Into this C4 mixture is metered an H2 stream of 3.5 Nl/h. 3 Nml/h CO is additionally added. After passage through the second reactor, butadiene is no longer detectable in the stream.

The invention claimed is:

1. A process for removing polyunsaturated hydrocarbons from an olefin-containing C4 hydrocarbon stream that, in addition to C4 hydrocarbons, also contains C5 hydrocarbons in a range between 0.01 and 5% by weight and mercaptans and/or disulfides in a range between 0.01 and 200 ppm by weight,
   wherein the process comprises a first step and a second step as follows:
   in the first step, at least some of the polyunsaturated hydrocarbons from the olefin-containing C4 hydrocarbon stream are hydrogenated and reacted with the mercaptans and/or disulfides from the olefin-containing C4 hydrocarbon stream in a first reaction zone in a presence of a molar ratio of hydrogen to polyunsaturated hydrocarbons between 0.01 and 0.8,
   wherein the first reaction zone comprises one or more reactors connected in parallel and/or in series,
   wherein the first step is carried out using a first catalyst comprising an alumina support material and a metal, where the metal comprises a combination of palladium and platinum having a palladium concentration of up to 2.0% by weight and a platinum concentration of up to 1.0% by weight,
   wherein the concentration of the palladium is at least a factor of 2 higher than that of platinum, wherein no carbon monoxide is added to the C4 hydrocarbon stream in the first step, and wherein not more than 80 mol % of the available polyunsaturated hydrocarbons from the C4 hydrocarbon stream are hydrogenated and reacted in the first step; and in the second step, remaining polyunsaturated hydrocarbons in the olefin-containing C4 hydrocarbon stream are selectively hydrogenated using a second catalyst in the presence of hydrogen and carbon monoxide in a second reaction zone, which comprises one or more reactors connected in parallel and/or in series;

wherein the second catalyst contains only a single metal of the 10th group of the periodic table, wherein the single metal is palladium; and wherein at least one removal of high boilers takes place between the first step and the second step.

2. The process according to claim 1, wherein the molar ratio of hydrogen to polyunsaturated hydrocarbons in the first step is between 0.1 and 0.5.

3. The process according to claim 1, wherein an inlet temperature of the C4 hydrocarbon stream in an inflow of the first reaction zone, is between 0° C. and 180° C.

4. The process according to claim 1, wherein the first step is carried out in a liquid phase and the hydrogen present has been dissolved in the liquid phase.

5. The process according to claim 1, wherein, in the second step, the content of carbon monoxide in the C4 hydrocarbon stream in the inflow of the second reaction zone, is 0.05 to 20 ppm based on a total amount of the hydrocarbon stream.

6. The process according to claim 1, wherein an inlet temperature of the C4 hydrocarbon stream in an inflow of the second reaction zone, is between 0° C. and 100° C.

7. The process according to claim 1, wherein a pressure in the second reaction zone, is in the range from 2 to 50 bar.

8. The process according to claim 1, wherein the second step is carried out exclusively in a liquid phase.

9. The process according to claim 1, wherein the first reaction zone comprises a single reactor.

10. The process according to claim 1, wherein the second reaction zone comprises at least two reactors connected in parallel or in series.

11. The process according to claim 1, wherein the at least one removal of high boilers is done with a distillation column having 40 to 100 theoretical plates and the distillation column has a reflux ratio of between 1 and 2.5.

12. The process according to claim 1, wherein an inlet temperature of the C4 hydrocarbon stream in an inflow of the first reaction zone, is between 60° C. and 150° C.

13. The process according to claim 1, wherein an inlet temperature of the C4 hydrocarbon stream in an inflow of the first reaction zone, is between 80° C. and 130° C.

14. The process according to claim 1, wherein an inlet temperature of the C4 hydrocarbon stream in an inflow of the second reaction zone, is between 20° C. and 80° C.

15. The process according to claim 1, wherein an inlet temperature of the C4 hydrocarbon stream in an inflow of the second reaction zone, is between 30° C. and 60° C.

16. The process according to claim 1, wherein a pressure in the second reaction zone, is in the range from 6 to 30 bar.

17. The process according to claim 1, wherein a pressure in the second reaction zone, is in the range from 10 to 25 bar.

18. The process according to claim 1, wherein the first catalyst comprises a palladium concentration of up to 1.0% by weight and a platinum concentration of up to 0.5% by weight.

19. The process according to claim 1, wherein the first catalyst comprises a palladium concentration of up to 0.5% by weight and a platinum concentration of up to 0.2% by weight.

20. The process according to claim 1, wherein the first catalyst comprises a palladium concentration of about 0.5% by weight and a platinum concentration of about 0.2% by weight.

21. The process according to claim 1, wherein the C4 hydrocarbon stream contains mercaptans.

22. The process according to claim 1, wherein the C4 hydrocarbon stream contains disulfides.

23. The process according to claim 1, wherein the C4 hydrocarbon stream contains mercaptans and disulfides and the C4 hydrocarbon stream reacts with the mercaptans and the disulfides.

24. The process according to claim 1, wherein the metal consists of the combination of palladium and platinum.

25. The process according to claim 1, wherein between the first and second step, at least some of the C5 hydrocarbons are removed from the C4 hydrocarbon stream.

* * * * *

UNITED STATES PATENT AND TRADEMARK OFFICE
CERTIFICATE OF CORRECTION

PATENT NO. : 11,952,340 B2
APPLICATION NO. : 16/713301
DATED : April 9, 2024
INVENTOR(S) : Peitz et al.

It is certified that error appears in the above-identified patent and that said Letters Patent is hereby corrected as shown below:

On the Title Page

Item (72), Line 1 in the INVENTORS currently reads:
"Der-Erkenschwick"
And should read:
--Oer-Erkenschwick--; and Under item (56), Column 2, Line 11 in OTHER PUBLICATIONS currently reads:
"U.S. Appl. No. 18/191,139, filed Mar. 28, 2023."
And should read:
--U.S. Appl. No. 18/191,139, filed Mar. 28, 2023, Peitz et al.--.

Signed and Sealed this
Eleventh Day of June, 2024

Katherine Kelly Vidal
*Director of the United States Patent and Trademark Office*